United States Patent [19]

Smith et al.

[11] Patent Number: 5,216,051

[45] Date of Patent: Jun. 1, 1993

[54] POLYOLEFINS CONTAINING POLYOL NUCLEATING AGENTS AND ARTICLES FORMED THEREFROM

[75] Inventors: Tammy L. Smith, Belle Mead, N.J.; Julie R. Schollmeyer, Des Plaines, Ill.; Yash P. Khanna, Cedar Knolls, N.J.; Kristina A. Miller, Budd Lake, N.J.; Divarakaran Masilamani, Morristown, N.J.

[73] Assignee: Allied-Signal Inc., Morristown, N.J.

[21] Appl. No.: 784,196

[22] Filed: Oct. 28, 1991

[51] Int. Cl.⁵ .............................................. C08K 5/15
[52] U.S. Cl. ............................. 524/108; 568/592; 568/598; 568/603; 568/590
[58] Field of Search ............... 524/377, 108; 568/23, 568/592, 598, 603, 590

[56] References Cited

U.S. PATENT DOCUMENTS

| | | | |
|---|---|---|---|
| 3,721,682 | 3/1973 | Murai et al. | 260/340 |
| 4,294,747 | 10/1981 | Su | 524/108 |
| 4,314,039 | 2/1982 | Kawai et al. | 524/108 |
| 4,408,650 | 2/1983 | Titus et al. | 524/108 |
| 4,431,759 | 2/1984 | Dusenbury et al. | 524/108 |
| 4,439,567 | 3/1984 | Inows et al. | 524/108 |
| 4,483,952 | 11/1984 | Uchiyama | 524/377 |
| 4,507,415 | 3/1985 | Kusai et al. | 524/101 |
| 4,845,137 | 7/1989 | Williams et al. | 524/108 |
| 4,902,807 | 2/1990 | Kobayashi et al. | 549/364 |
| 5,001,176 | 3/1991 | Nakazima et al. | 524/48 |
| 5,049,605 | 9/1991 | Rekers | 524/108 |

Primary Examiner—Paul R. Michl
Assistant Examiner—Sid Kalachandra
Attorney, Agent, or Firm—Darryl L. Webster; Richard C. Stewart; Gerhard H. Fuchs

[57] ABSTRACT

The invention relates to novel tri-acetal polyol compounds and to a crystalline polyolefin composition having dispersed therein a nucleating agent composed of one or more of said polyol acetals.

38 Claims, 5 Drawing Sheets (R)

(S)

POLYOLEFINS CONTAINING POLYOL NUCLEATING AGENTS AND ARTICLES FORMED THEREFROM

BACKGROUND OF THE INVENTION

1. Field of the Invention

This invention relates to novel polyol acetal compounds which are useful as nucleating agents for polyolefins. This invention also relates to polyolefin based compositions containing the polyol acetal compounds. Another aspect of this invention relates to articles of manufacture formed totally or in part from the polyolefin based composition of this invention.

2. Description of the Prior Art

The "super" or morphological structure in which the crystalline units are arranged, affects the physical properties of polyolefins. The crystalline units are arranged in polycrystalline aggregates known as spherulites. These spherulites may be detected by microscopic examination under polarized light. They are characterized by a more or less symmetrical growth in all directions from a nucleus and are composite structures made up of crystalline and amorphous regions. The number and size of the spherulites determines the texture or graininess in the bulk of the material and influences optical as well as physical properties. Physical properties improve with increasing homogeneity and fineness of the spherulitic structure throughout the bulk of the material.

To obtain optimum physical properties in articles fabricated from polyolefins, it is desirable, therefore, to produce a highly crystalline material, crystallized with an extremely fine, dense and uniform morphological structure.

Among the physical properties affected by increased crystallinity and improved morphological structure are abrasion resistance, heat distortion temperature, inherent stability or resistance to deformation, resistance to hot water, coefficient of expansion, hardness, tensile yield strength and surface hardness.

Nucleation by foreign materials has been extensively studied, especially in the case of polypropylene. For example, H. N. Beck or H. D. Led better, *J. Appl. Polym. Sci.* 9, 2131 (1965) and H. N. Beck, *J. Appl. Polym. Sci.* 11,673 (1987) checked the nucleation activity of more than two hundred substances by determining the temperature, Tcc, at which the crystallization rate on cooling is the fastest. F. L. Binsbergen, Polymer, 11, 253 (1970) extended these studies in testing two thousand substances for nucleating activity in polyethylene, polypropylene, poly(4-methyl-1-pentene) and poly(styrene). Other working nucleating agents for polyolefin are described on J. P. Mercier, *Polymer Engineering and Science*, 30, 270 (1990), Wijga, P. W. O. U.S. Pat. No. 3,207,735; —6; —8(1960) Wijga, P. W. O. and Binsbergen, F. L. U.S. Pat. No. 3,299,029(1961) Wales, M. U.S. Pat. No. 3,207,737;—(1961–62) Binsbergen, F. L. U.S. Pat. Nos. 3,326,880; 3,327,020;—1(1963) Kargin, V. A. et al, *Dokl. Akad. Nauk.* SSSR 1964, 156, 1156(transl.: Dokl. Phys. Chem, 1964, 156, 621, 644) Doring, C. and Schmidt, H. German Pat. (Federal Rep.) 1,188,279(1963) and Vonk, G. C. Kolloid Z. 1965, 206, 121.

The function of nucleating agents when cooling semicrystalline polymers from the molten state into the solid form is to increase the number of nuclei formed in a given time interval at a predetermined temperature. The final and overall crystallinity, however, depends not only on the number of nuclei that are formed but also on the spherulitic growth rate from such nuclei. As noted above, spherulites develop with respect to a center, or nucleus, of growth. Addition of the nucleating agents thus provides a large number of sites for growth upon cooling from a melt. In order to be of practical use, such nucleating agents not only must produce a fine spherulitic structure but also must do this under conditions of rapid cooling to a temperature above the glass transition temperature of the polyolefin, i.e., they must reduce the time that is necessary under a given set of conditions for crystallization to start. This time is usually referred to as "induction time". Subsequent growth from the spherulitic center depends on the polymer chain mobility. Thus, a factor in the spherulitic growth rate is the macroscopic viscosity of the polymer and its temperature dependence. All segmental motion is "frozen in" at the glass transition temperature (Tg) and no additional crystallization occurs even when nuclei are present. This Tg is about $-20°$ C. in polypropylene.

Much of the art relating to polyol acetals relates to the use of dibenzylidene sorbitol compounds as additives in various polyolefins. U.S. Pat. No. 3.948,946 to Hofer et al; U.S. Pat. No. 4,016,118 to Hamada; U.S. Pat. No. 4,294,747 to Su; and U.S. Pat. No. 4,371,645 to Mahaffe4y, Jr. are exemplary of polyol acetal compounds known in the art.

SUMMARY OF THE INVENTION

Presently, it has been discovered that the crystallization temperature ($T_{cc}$) of polyolefin can be increased by the addition of an effective amount of one or more tri-acetal polyols. The crystallization temperature upon cooling reflects the overall crystallization rate due to the combined effects of nucleation and growth of crystallites/spherulites. A non-nucleated polymer would have a lower $T_{cc}$ than a nucleated material, and a polymer crystallizing at a lower rate would have a lower $T_{cc}$ than a faster crystallizing polymer. It is believed that an increase in $T_{cc}$ and the corresponding increase in the crystallization rate indicate an improvement in the thermal, optical and/or mechanical properties of the polymer. See "Memory Effects in Polymers II. Processing History vs. Crystallization Rate of Nylon 6-Observation of Phenomenon and Product Behavior", Y. P. Khanna et al. in *Polymer Engineering and Science*, 24, Vol. 28, pp. 1600–1606, December, 1988, and also "Memory Effects in Polymers III", Y. P. Khanna et al. in *Polymer Engineering and Science*, 24, Vol. 28, pp. 1607–1611, December 1988, for additional information regarding the effects of increasing the $T_{cc}$ of a polymer.

In accordance with this invention, there are provided novel tri-acetal polyols, polyolefin based compositions containing the tri-acetal polyols and articles formed from such compositions. The tri-acetal polyols function as nucleating agents to provide for a relatively homogeneous and fine spherulitic or crystal structure when dispersed in a polyolefin composition. More particularly, the composition of this invention comprises:

one or more polyolefins; and effective amount of one or more nucleating polyols acetals.

Yet another aspect of this invention relates to a novel process for enhancing the rate of crystallization of a polyolefin from the melt, which comprises adding to said polyolefins a crystallization enhancing active amount of the nucleating agent of this invention.

Several advantages flow from this invention. For example, by speeding up the rate of crystallization, processing times are decreased. Moreover, the polyolefins formed in accordance with this invention are characterized by relatively improved thermal, optical or mechanical properties.

BRIEF DESCRIPTION OF THE DRAWINGS

The invention will be more fully understood and further advantages will become apparent when reference is made in the following detailed description of the invention and the accompanying drawings in which.

DESCRIPTION OF THE EMBODIMENTS OF THE INVENTION

Figure 4A:
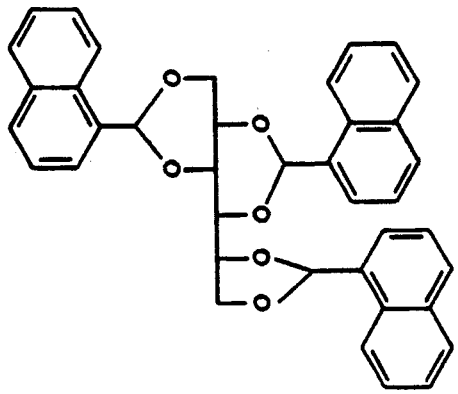
FIG. 4 is a diagram of several of the tri-acetal polyol compounds of this invention.
Figure 4B:
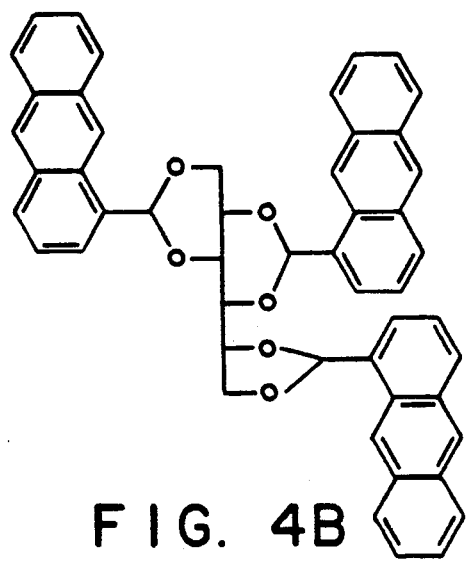
Figure 4C:
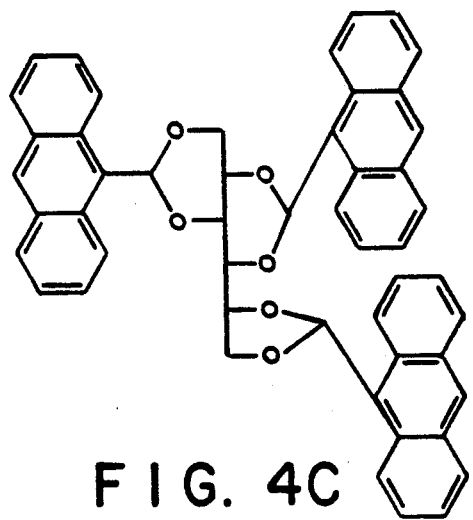

The novel tri-acetal polyols compounds of this invention are a polyol/aldehyde condensates wherein each of the acetal moieties contains a —CH— group to which two oxygens of the polyol are attached to form the tri-acetal polyols. FIG. 4 depicts some of the novel tri-acetal polyols of this invention. The acetal moiety is derived from an aldehyde having the following formula:

I wherein:

A is a monovalent hydrocarbon radical.
Preferably, the hydrocarbon radical contains about 50 carbons or less. More preferably, the hydrocarbon radical contains about 25 carbons or less.

In alternative embodiments the tri-acetal polyol compounds are formed from aldehydes of Formula I wherein A monovalent radical is derived from a monocyclic or polycyclic compound. Preferably, A is a monovalent hydrocarbon radical derived from an aromatic containing compound. In preferred embodiments, A is a monovalent radical derived from aromatic or heteroaromatic compounds wherein ring hydrogens of said compounds are substituted with one or more of X; wherein X is selected from one of the following —OH, —SH, —OR, SR, R, —CL, —Br, I, Fl, —COOH and COOR, R being a hydrocarbon radical having up to about 20 carbons. In the preferred embodiments of the invention, X is selected from one or more of —OH, —SH, —OR, —SR, —R, —Cl, —Br, —I, —Fl, —COOH and —COOR, wherein R is an alkyl, cyclo alkyl, halogenated alkyl and hereto containing cycloalkyl. In more preferred embodiments X can be —OH, —SH, —OR, —SR, —R, —Cl, —Br, —I, —Fl, —COOH and —COOR, wherein R is alkyl having from 1 to about 12 carbons. In further embodiments, X is selected from OH, —SH, —OR, —SR, —R, Cl, Br, I, Fl, —COOH and —COOR and R is an alkyl substituent having from 1 to about 8 carbons. In particular preferred embodiments, X and R, are as described in the above further preferred embodiments except R is an alkyl having 1 to about 6 carbons, with 1 to about 4 carbons being the range of choice for the R substituent.

In alternatively preferred embodiments A is a monovalent hydrocarbon radical derived from an unsubstituted or substituted polycyclic aromatic compound. In such embodiments, preferably, A is derived from a polycyclic aromatic compound in which the polycyclic compound has at least two rings fused together and at least one of the ring structures is an aromatic ring. The aromatic ring can be a heterocyclic aromatic or non-heterocyclic aromatic ring; however, preferably, at least one ring member is a benzene group. In particularly preferred embodiments, the polycylic compound comprises at least two aromatic rings fused together. The number of ring structures in the polycyclic aromatic compound ranges from 2 to about 10. In preferred embodiments the number of rings ranges from 2 to about 6. In more preferred embodiments, the number of rings ranges from 2 to about 5. In particularly preferred embodiments, the number of rings range from 2 to about 4.

Illustrative of polycyclic aromatic compounds which may be used to form the acetal moiety of the polyol acetal include compounds wherein A is a monovalent radical derived from compounds such as naphthalene, phenanthrene, anthracene, quinoxaling, fluorene, benzofuran and quinolines. The non-hetero aromatics are generally preferred over hetero aromatics. Naphthalene is especially preferred.

The hydrogens of the ring members of the monocyclic or polycyclic monovalent radical may be substituted with X; wherein X is selected from one or more of the following —OH, —SH, —OR, —SR, —R, —CL, —Br, —I, —Fl, —COOH, —COOR, R being a hydrocarbon radical having up to about 20 carbons. In the preferred embodiments of the invention, X is selected from one or more of —OH, —SH, —OR, —SR, —R, —Cl, —Br, —I, —Fl, —COOH and —COOR, wherein R is an alkyl, cycloalkyl, halogenated alkyl and hetero-containing cycloalkyl. In more preferred embodiments, X can be —OH, —SH, —OR, —SR, —R, —Cl, —Br, —I, —Fl —COOH and —COOR, wherein R is alkyl having from 1 to about 12 carbons. In further embodiments, X is selected from OH, —SH, —OR, —SR, —R, Cl, —Br, —I, —Fl, —COOH and —COOR and R is an alkyl substituent having from 1 to about 8 carbons. In particular preferred embodiments, X and R, are as described in the above further preferred embodiment except that R is an alkyl having 1 to about 6 carbons, with 1 to about 4 carbons being the range of choice for the R substituent.

In additional embodiments of the invention, A of Formula I is a monovalent radical derived from acyclic compounds. Preferably, the acyclic compounds are compounds having about 20 carbons or less. More preferably, the acyclic compounds are alkanes, alkenes or alkynes. In further preferred embodiments, the acylcic compounds are alkanes, alkenes or alkynes having about 12 carbons or less.

It is noted that the tri-acetal polyols of this invention may also be a condensation product of a polyol and two or more different aldehydes. For example, a polyol condensed with one or more aldehydes derived from a polycyclic compound may also be reacted with one or more monocyclic or acyclic aldehydes to form additional acetal moieties (the polycyclic moiety may be formed before or after the monocyclic or acyclic polyol/aldehyde condensation as needed). The monocyclic or acyclic aldehydes which form the acetal may also contain substituent groups selected from X; wherein X is selected from one or more of the following —OH, —SH, —OR, —SR, —R, —CL, —Br, —I, —Fl, —COOH, —COOR, R being a hydrocarbon radical having up to about 20 carbons.

Preferably, when A of Formula I is derived from monocyclic compounds, the compounds are selected from aromatic containing groups (hetero or non-heterocyclic aromatics), cycloalkyl and cycloalkenyl groups. In more preferred embodiments, the monovalent radical is derived from a monocyclic compound having a substituted or unsubstituted aromatic ring. In particularly preferred embodiments, the aromatic ring of the monocyclic aldehyde is substituted with one or more selected from hydroxyl, halogen, alkoxy, mercapto, halogenated alkyl, hydroxy alkyl, alkylthio or alkyl. In more particularly preferred embodiments, the monocyclic aldehyde is a benzene ring which is substituted with one or more substituents selected from hydroxy, alkyl, halogen, halogenated alkyl, hydroxy alkyl, alkylthio, mercapto or alkyl, said substituent having up to about 10 carbons, with the substituents of choice having up to about 6 carbons.

The polyols used to form the polyol moiety of the polyol acetal may vary widely. The polyols include, generally, any polyhydroxy compound which can be reacted with an aldehyde to form an acetal. Preferably, the polyol is acyclic. The number of carbons in the polyol can vary substantially. Specific properties which are desired will be determined by the number of carbons as well as the number of hydroxy substituents. A list the preferred ranges for the number of carbons is provided below. The more preferred ranges are listed last with the final range being the range of choice.

Ranges for Number of Carbons in Polyol

6–20
6–15
6–12
6–10
6–8

For each of the above ranges, the number of hydroxyl substitutents will vary also. The number of hydroxyl substituents vary by the number of acetal moieties desired and the number of additional hydroxyls substituents desired on the polyol acetal. Illustrative of polyols useful in the practice of this invention are polyols formed from reduction of aldoses and ketoses which have at least 6 carbons and 6 hydroxyl groups.

Preferably, the polyols used in the practice of this invention are reduced sugars having 6 carbons. Polyols derived from reduced sugars include sorbitol, mannitol and galactitol. In preferred embodiments, the polyol is sorbitol.

When the condensation of a polyol and aldehyde forms a tri-acetal with one acetal being a five membered ring, the compound will be isomeric. Sorbitol generally forms a tri-acetal in the 1,3;2,4;5,6 position, in which the 5,6 acetal is a 5-membered ring. An illustrative example of the isomers of tri-acetal polyols is depicted at FIG. 5.

The tri-acetal polyol isomer preferred in this invention is the isomer (herein referred to as isomer$_1$) which increases the crystallization temperature ($T_{cc}$) of a polyolefin more than the other isomer (herein referred to as isomer$_2$) when added to the same amount of polyolefin in equal amounts. The isomers can be selected based on their respective NMR spectra. The isomers will have differing chemical shifts based on the hydrogens of the —CH— group of the acetals of the isomer. Once characterized by NMR, the isomer of choice can be selected and employed as needed. It is theorized that in most instances isomer$_1$ has a downfield shift for each hydrogen of the —CH— group of each acetal. For further details on the NMR of tricetal polyols, see Brecknell et al. "Tri-benzylidene-Dglucitol", *Aust. J. Chem.* 29, 1859 (1976). The isomers can also be recognized and separated based on their melting points. Once separated, isomer$_1$ is detected by comparing the $T_{cc}$ of polyolefin compositions when each isomer is added. Procedures for separation include conventional techniques known in the art for separating compounds based on their melting points.

In alternatively preferred embodiments of this invention, the tri-acetal compounds are selected from those which form isomers. In more preferred embodiments, a mixture of isomers is employed wherein at least 5 percent of the mixture comprises isomer$_1$. In further preferred embodiments, a mixture of isomers is employed wherein at least 15 percent of the mixture comprises isomer$_1$. In particularly preferred embodiments, a mixture of isomers is employed wherein at least 15 percent of the mixture comprises isomer$_1$. In more particularly preferred embodiments, a mixture of isomers is employed wherein at least 50 percent of the mixture comprises isomer$_1$. For such mixtures, it is further preferred to use a mixture comprising at least about 75% of isomer$_1$ with a mixture of choice having at least about 85 percent of isomer$_1$.

Figure 5A:
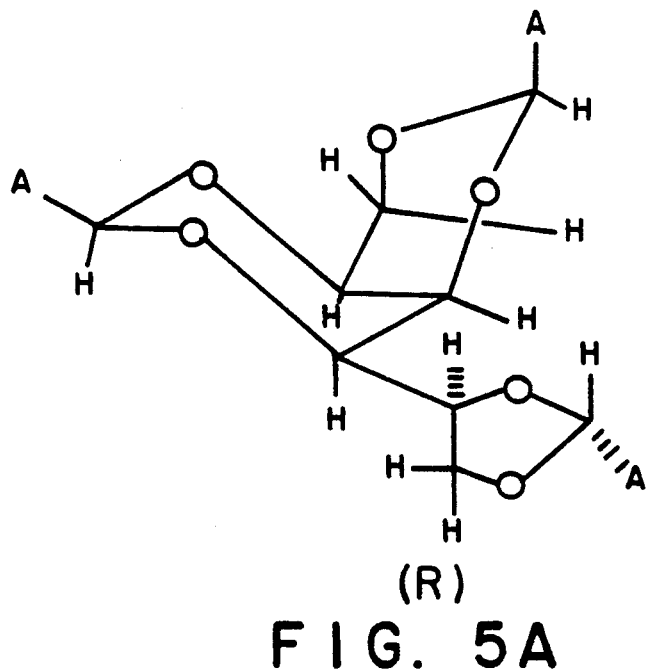
FIG. 5 is a diagram of several of the isomers of tri-acetal polyol compounds wherein A is as described in the Description of the embodiments.
Figure 5B:
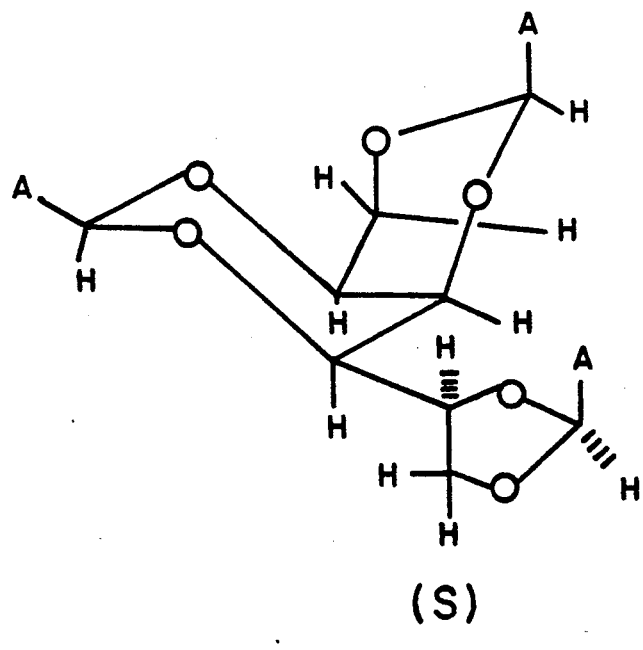

As depicted in FIG. 5, the isomer can be "R" or "S". It is believed that isomer$_1$ is the "S" isomer.

The nucleating tri-acetal polyols of this invention can be prepared by conventional means. Generally, acetals of a polyol are formed by the addition of the polyol, e.g. reduced sugar, to an appropriate aldehyde in the presence of an acid catalyst. The appropriate aldehyde is the aldehyde derivative of the polycyclic, monocyclic or acyclic compound desired to form the acetal moiety of the acetal polyol. Various solvents can be employed in this reaction. It is prefered to use a solvent system in which the polyol and aldehyde are soluble. Polar aprotic solvents can be added to increase polyol solubility. Examples of suitable solvents include but are not limited to water, cyclohexane, hexane, benzene dichloromethane, tetrahydrofuran, dimethyl sulfoxide, acetonitrile and dimethyl formamide. In addition, the acid employed can vary substantially. Any protic acid will suffice. Acid is necessary as a catalyst. Illustrative of acids for use in the practice of the invention include sulfuric acid, hydrochloric acid, p-toluenesulfonic, trifluoroacetic acid and methane sulfonic acid. The synthesis reaction can be run at room temperature(about 23° C.) or can be heated above 23° C. The reaction temperature can be below 23° C., but the reaction rate is believed to decrease at temperatures below about 23° C. The reaction rate is accelerated at high temperatures- (above 23° C.). It is noted that running the reaction in a non-miscible solvent with water allows water to be removed upon distillation as an azeotrope. Water can additionally be removed by the addition of molecular sieves. Removal of water shifts the equilibrium of the reaction towards the product and is desirable.

Another aspect of this invention relates to polyolefin compositions which comprise one or more polyolefins and an effective amount of one or more triacetal polyols. Illustrative of polyolefins for use in the practice of this invention are those formed by the polymerization of olefins of the formula:

wherein:

$R_1$ and $R_2$ are the same or different and are hydrogen or substituted or unsubstituted alkylphenyl, cycloalkyl, phenylalkyl, phenyl, or alkyl. Useful polyolefins include polystyrene, polyethylene, polypropylene, poly(1-octadecene), polyisobutylene, poly(1-pentene), poly(2-methylstyrene), poly(4-methylstyrene), poly(1-hexene), poly(5-methyl-1-hexene), poly(4-methylpentene), poly(1-butane), poly(3-methyl-1-butene), poly(3-phenyl-1-propene), polybutylene, poly(methyl pentene-1), poly(1-hexene), poly(5-methyl-1-hexene), poly(1-octadecene), poly(vinyl cyclopentane), poly(vinylcyclohexane), poly(a-vinylnaphthalene), and the like.

Preferred for use in the practice of this invention are polyolefins of the above referenced formula in which R is hydrogen or alkyl having from 1 to about 12 carbon atoms such as polyethylene, polypropylene, polyisobutylene, poly(4-methyl-1-pentene), poly(1-butene), poly(1-pentene), poly(3-methyl-1-butene), poly(1-hexene), poly(5-methyl-1-hexene), poly(1-octene), and the like.

In the particularly preferred embodiments of this invention, the polyolefins of choice are those in which $R_1$ is hydrogen and $R_2$ is hydrogen or alkyl having from 1 to about 8 carbon atoms such as polyethylene, polypropylene, poly(1-hexene), poly-1-butene, poly-1-pentene, poly-1-heptene, poly(4-methyl-1-pentene), and poly(1-octene). Amongst these particularly preferred embodiments, most preferred are those embodiments in which $R_1$ is hydrogen and $R_2$ is hydrogen or alkyl having from 1 to about 6 carbon atoms such as polyethylene, polystyrene, polypropylene, poly(4-methyl-1-pentene), and polyisobutylene, with polypropylene being the polyolefin of choice.

The amount of polyolefin included in the composition of the invention may vary widely and is usually from about 99.99 to about 90.00 percent by weight based on the total weight of the composition. In the preferred embodiments of this invention, the amount of polyolefin is from about 99.99 to about 95.00 weight percent based on the total weight of the composition; and in the particularly preferred embodiments of the invention the amount of polyolefin in the composition is from about 99.90 to about 99.0 weight percent based on the total weight of the composition. Amongst the particularly preferred embodiments, most preferred are those embodiments in which the amount of polyolefin is from about 99.90 to about 99.5 percent by weight based on the total weight of the composition.

Polyolefins for use in the practice of this invention may be obtained from commercial sources or prepared in accordance with known preparatory techniques. For example, useful polyolefins, such as polypropylene, polystyrene, polyethylene and poly(4-methyl-1-pentene) can be obtained commercially as for example ICI Ltd, and Dupont Co. Such polyolefins can also be prepared by a low temperature process using an organic metallic catalyst, as for example those described in Belg. Pat 533,362 and U.S. Pat. No. 2,691,647 which are hereby incorporated by reference.

The molecular weight of the polyolefin may vary widely. For example, the polyolefin may be a wax having a relatively low molecular weight i.e., 500 to 1,000 or more. The polyolefin may also be melt spinnable and of fiber forming molecular weight. Such polyolefins for use in the practice of this invention are well known. Usually, the polyolefin is of fiber forming molecular weight having a molecular weight of at least about 5,000. In the preferred embodiments of the invention the molecular weight of the polyolefins is from about 8,000 to about 1,000,000 and in the particularly preferred embodiments is from about 25,000 to about 750,000. Amongst the particularly preferred embodiments most preferred are those in which the molecular weight of the polyolefins is from about 50,000 to about 500,000.

The amount of nucleating agent added to the polyolefin is an "effective amount". As used herein, an "effective amount" is an amount which is sufficient to improve the homogeneity and/or fineness of spherulitic structures in the polyolefin to any extent. Such amounts will normally correspond to amounts of conventional nucleating agents. In the preferred embodiments of the invention, the amount of nucleating agent employed is in the range of from about 0.15 to about 1 weight percent based on the total weight of polyolefin and agent, and in the particularly preferred embodiments of the invention is from about 0.2 to about 0.6 weight percent on the aforementioned basis. Amongst these particularly preferred embodiments, most preferred are those embodiments where the amount of nucleation agent employed is from about 0.25 to about 0.5 weight percent based on the total weight of agent and polyolefin.

In addition to the above-described essential components, the molding composition of this invention can include various optional components which are additives commonly employed with polyester and polyolefin resins. Such optional components include fillers, plasticizers, impact modifiers, chain extenders, colorants, mold release agents, antioxidants, ultra violet light stabilizers, lubricants, antistatic agents, fire retardants, and the like. These optional components are well known to those of skill in the art, accordingly, only the preferred optional components will be described herein in detail.

A filler can be added to increase the modulus and stiffness of the composition, and provide a more economical composition. Any conventional fibrous or particulate filler can be employed provided that it provides all or a portion of the above-identified functions, and does not otherwise have a deleterious effect on the composition. The fillers may optionally be treated with various coupling agents or adhesion promoters as is known to those skilled in the art. Useful fillers may be selected from a wide variety of minerals, metals, metal oxides, siliceous materials, metal salts, and materials thereof. Examples of such useful fillers include alumina, aluminum hydrates, feldspar, asbestos, talc, calcium carbonates, clay, carbon black, glass quartz, novaculite and other forms of silica, kaolinite, bentonite, garnet, mica, saponite, beidellite, calcium oxide, calcium hydroxide, and the like. Such fillers are well known materials and are readily available. The foregoing recited fillers are illustrative only and are not meant to limit the scope of the fillers that can be employed in this invention. Fibrous materials such as fiber glass, carbon fibers, boron fibers and polymer fibers are the fillers of choice, and the glass fibers is the filler of choice in the particularly preferred embodiments of this invention.

The quantity of filler employed is not critical and can be varied widely as desired. In the preferred embodiments of this invention, the quantity of filler is up to about 150 weight percent based on the total weight of the polymer component, and in the particularly preferred embodiment is in the range of from about 30 to about 90 weight percent on the same basis.

While not essential, it may be desirable to include an optional plasticizer in the composition of this invention. The plasticizer allows crystallization of the amorphous areas of the composition to continue at lower temperatures than if a plasticizer is not used. This is particularly important in low temperature molding. The plasticizers which can be used with the composition of the present invention are of the type known in the art as useful in lingar polyolefin molding compositions. Such useful plasticizer compositions are well known in the art and accordingly will not be described herein in detail.

The composition of this invention can be further modified by the addition of one or more pigments. Illustrative of useful pigments are iron oxide, cadmium red, rhodaming, chrome yellow, chrome green, and phthalocyanine blue.

The composition of this invention can be prepared by blending or mixing the essential ingredients, and other optional components, as uniformly as possible employing any conventional blending means. Appropriate blending means, such as melt extrusion, batch melting and the like, are well known in the art and will not be described here in greater detail. In one useful procedure, the blending procedure can be carried out at elevated temperatures above the melting point of the polymer and the nucleating agent added either alone or as individual components of the agent separately or as a combination of the components in a suitable form as for example, granules, pellets and preferably powders are added to the melt with vigorous stirring. Alternatively, all or a portion of the various components of the nucleating agent can be masterbatched or preblended with the polyolefin in the melt and this premixed or masterbatch added to the polyolefin in the melt in amounts sufficient to provide the desired amount of nucleating agent in the polyolefin product. Stirring is continued until a homogeneous composition is formed. The nucleating agent can also be added to the melt coated on the surface of small particle inert powders which have a high surface to volume ratios. The use of such inert powders, as for example, fused silica, fused alumina, carbon black and aerogels, and hydrogels of silica or alumina, helps to reduce the amount of nucleating agent required to provide optimum results. Blending pressures, and the order of addition of the various components are not critical and may be varied as desired provided that a substantially homogeneous composition results. The blending procedure can be carried out at elevated temperatures, in which case the polymer component is melted and the solid nucleating agent is admixed therewith by vigorously stirring the melt. Similarly, the various solid components can be granulated, and the granulated components mixed dry in a suitable blender, or for example, a Banbury mixer, as uniformly as possible, then melted in an extruder and extruded with cooling.

Alternatively, the composition of this invention can be formulated by dissolving the components in an appropriate inert solvent, after which the solvent is removed by evaporation, or other conventional solvent removing means are employed to provide the composition. The solvent is not critical, the only requirement being that it is inert to the components of the composition, and it is capable of solubilizing the various components, or at least forming dispersions thereof.

The compositions according to the invention can be partially crystalline to amorphous, depending on which individual constituents are employed. They are thermoplastic materials from which molded articles of manufacture having valuable properties can be produced by the conventional shaping processes, such as melt spinning, casting, injection molding and extruding. Examples of such moldings are components for technical equipment, apparatus casting, household equipment, sports equipment, components for the electrical and electronics industries and electrical insulations, car components, circuits, fibers, and semi-finished products which can be shaped by machining. The molding compositions according to the invention are outstandingly suitable for specific applications of all types since their spectrum of properties can be modified in the desired direction in many ways.

The compositions according to the invention are outstandingly suitable for the production of sheets and panels having valuable properties. The sheets and panels according to the inventions are suitable as coating materials for other materials comprising, for example, wood, glass, ceramic, metal or other plastics, and outstanding strengths can be achieved using conventional adhesion promoters, for example, based on vinyl resins. The sheets and panels can also be laminated with other plastic films and this is preferably effected by joint extrusion, the sheets being bonded in the molten state. The surfaces of the sheets and panels, including those in the embossed form, can be improved or finished by conventional methods, for example by lacquering or by the application of protective films. The compositions of this invention are especially useful for fabrication of extruded films, as for example films for use in food packaging.

EXAMPLES

Synthesis-Trinaphthylidene Sorbitol

1-Naphthaldehyde (85.00 g) and D-sorbitol (33.05 g) were combined with water (14.5 mL), dimethylsulfoxide (23 mL), cyclohexane (700 mL), and methane sulfonic acid (2.2 mL) and heated under nitrogen to reflux. (The mono acetal is formed first but it comes back into solution as the reaction continues). Water was removed by distillation. Heating was stopped after water distillation was complete. At this point the reaction product is mainly composed of the "S" isomer. Further heating tends to increase the amount "R" isomer in the product. The product was filtered from the reaction mixture, washed with aqueous $Na_2CO_3$, and purified by a solid/liquid extraction with a tetrahydrofuran/aqueous $NaHCO_3$ (1:25:1) solution to yield pure 1,3;2,4;5,6 trinaphthylidene sorbitol (58.4 g).

Other tri-acetal polyol compounds tested were prepared following the above procedure, except that the aldehyde was varied to form the desired compound. The heating step was also varied and the amounts of each isomer present were measured.

I. GENERAL PROCEDURE

A. Melt-Mixing Procedure

About 25 mg (0.5%) of powdered additive trinaphthylidene sorbitol was added to 5 gm of the powdered isostatic polypropylene and tumble mixed on a roll mill. This mixture was fed into the reservoir of an Instron Capillary rheometer, equilibrated at 180° C. for 5 minutes, and then extruded into strands of about 3 mm diameter. The strands were chopped into pieces (0.25" long) and subsequently re-extruded under the same conditions in order to provide a better dispersion of the additive in the polymer. Polypropylene alone was also treated similarly to obtain a control sample. The loading of the additives was 0.5% unless otherwise noted.

B. Solution-Mixing Procedure

About 5 mg (0.5%) of the powdered additive was added to 1 gm of the powdered isostatic polypropylene and refluxed with 10 gm of dichlorobenzene at 180° C. for about 16 hours. The solution was then quick-cooled under tap water and the dispersion of additive/polypropylene recovered by filtration. The samples were dried under high vacuum at about 130° C. Polypropylene alone was also treated similarly to obtain a control sample.

C. Differential Scanning Calorimetry (DSC)

An automated DuPont 9900 DSC operating in an argon atmosphere was used for analysis. About 10($\pm$1) mg sample was crimped in an aluminum cup, heated from 0° C. to 200° C. at a rate of 20° C./min., held at 200° C. for 5 min., and then subsequently cooled at a rate of 10° C./min. The data is represented as a crystallization temperature upon cooling ($T_{cc}$°C.).

Selected samples were also analyzed by isothermal DSC. In these experiments, the samples were cooled to 135° C. and isothermally crystallized at 135° C./4 hours following the 200° C./5 min. treatment.

C. Optical Microscopy

The samples crystallized in the DSC isothermally at 135° C. for 4 hours, were cross-sectioned and the photomicrographs prepare in transmitted polarized light.

D. Isomer Separation

Using HPLC separation was achieved as follows:

| | |
|---|---|
| Instrument: | MP 1090 Liquid Chromatograph equipped with a diode-array detector |
| Column: | Chromegabond DNAP, 5 μm, 300Å, 250 × 4.6 mm I.D. |
| Mobile Phase: | 40% methylene chloride in heptane programmed to 60% methylene chloride in 20 minutes. |
| Flow Rate: | 2 ml/min |
| Detection: | UV at 254 nm |
| Injection Volume: | 50 μl of 0.1% solution methylene chloride/heptane |

II. DESCRIPTION OF EXAMPLES

Example A

Using the melt-mixing procedure, trinaphthylidene sorbitol was dispersed in polypropylene and the following results were measured using DSC:

| Mass % | Crystallization Temperature of Polypropylene ($T_{cc}$, °C.) |
|---|---|
| 0.00 | 110 |
| 0.10 | 112 |
| 0.25 | 112 + 124** |
| 0.40 | 123 |
| 0.50 | 123, 124* |
| 0.60 | 121 |
| 0.75 | 121 |
| 1.00 | 119 |

**-two crystallization peaks were observed and are believed to be caused by human error in mixing the additive with the polymer.
*-two separate runs were conducted.

Example B

The following were dispersed in polypropylene following the melt-mixing procedure. Crystallization temperatures were measured with DSC.

| Compound | Mass % | $T_{cc}$ (°C.) of Polypropylene |
|---|---|---|
| None | 0.00 | 109 |
| Tribenzylidene Mannitol | 0.50 | 117 |
| Trinaphthylidene Sorbitol isomer | | |
| 1 | 0.50 | 122.4 |
| 2 | 0.50 | 113 |
| 1/2 (48/52) | 0.50 | 110 |
| 1/2 (45/55) | 0.50 | 116 |
| 1/2 (20/80) | 0.50 | 121 |
| 1/2 (13/87) | 0.50 | 124,125* |
| 1/2 (5/95) | 0.50 | 124 |
| Tri(4-methoxy-1-Naphthylidene Sorbitol 1/2 (84/16) | 0.50 | 119 |
| Tri(4-methyl-1-naphthylidene) Sorbitol: 1/2 (10/90) | 0.50 | 122 |
| Tri-(4-isopropyl-benzylidene) Sorbitol: 1/2 (84/16)* | 0.50 | 119 |
| Naphthylidene Sorbitol | 0.25 | 117 |
| Dinaphthylidene Sorbitol | 0.50 | 111 |
| Millad 3905 | 0.50 | 123.1 |

The numbers 1 & 2 in the above examples refer to isomer$_1$ and isomer$_2$.
*this mixture was determined to have 84% of at least one isomer, which is beleived to be isomer$_1$.

COMPARATIVE EXAMPLE

The isothermal crystallization rate was measured for polypropylene containing no additives, for polypropylene containing trinaphythylidene sorbitol and polypropylene containing commercial clarifier Millad 3905 (available from Milliken).

| Additive | Crystallization Rate $t_{.05}^{-1}$ min$^{-1}$, ×1000 |
|---|---|
| NONE | 15 |
| 0.50 (TNS-isomer$_1$) | 208 |
| 0.50 (Millad 3905) | 88 |

Figure 1:
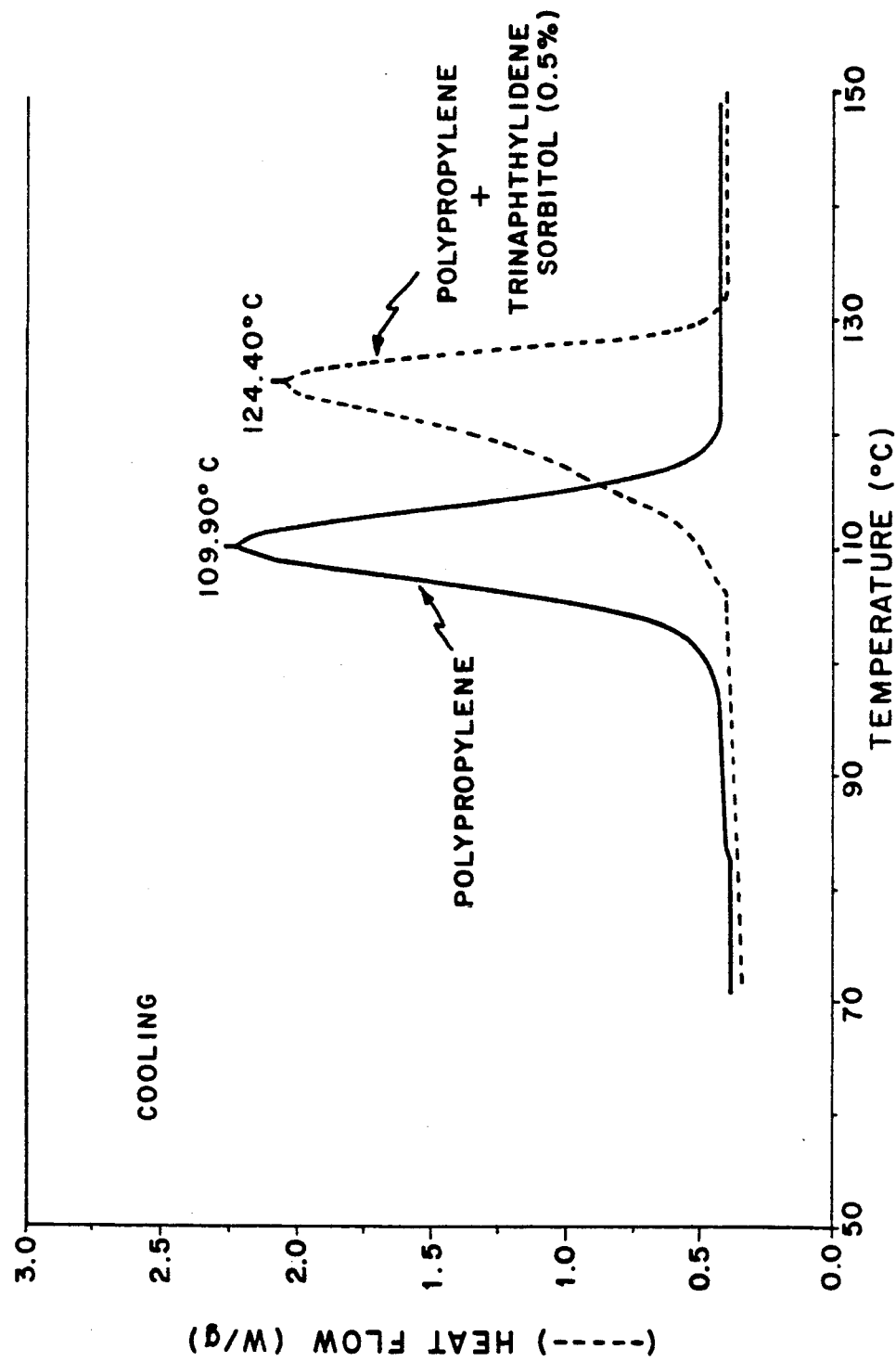
FIG. 1 is a Differential Scanning Calorimetry thermogram showing the effect of 0.5% by weight of trinaphthylidene sorbitol on the crystallization of polypropylene.
Figure 2:
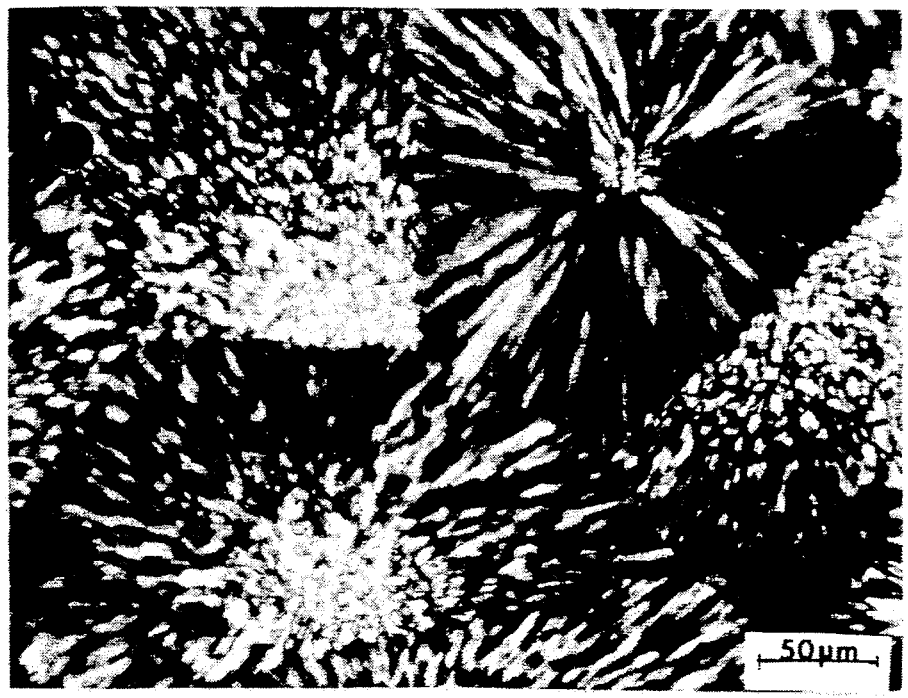
FIG. 2 is an optical photomicrograph of polypropylene which does not contain a nucleating agent crystallized in a differential scanning calorimeter at 135° C.
Figure 3:
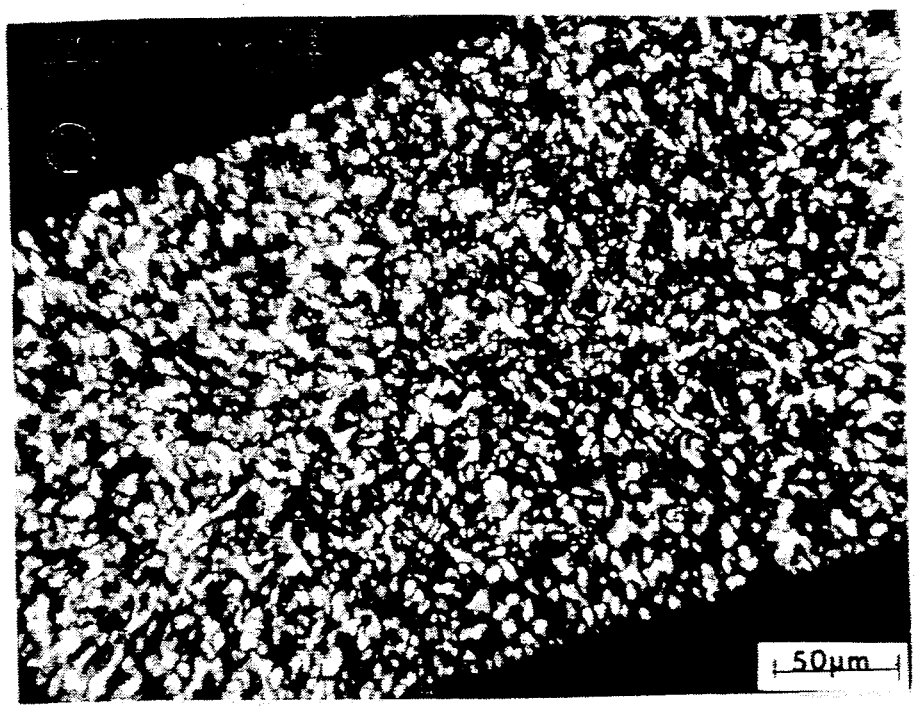
FIG. 3 is an optical photomicrograph of polypropylene which contains 0.5% by weight trinaphthylidene sorbitol nucleating agent crystallized in a differential scanning calorimeter at 135° C.

See also FIG. 1 which shows that the crystallization peak of polypropylene occurs at a significantly higher temperature and the peak is much sharper for the polypropylene containing trinaphthylidene sorbitol. In addition, the electron micrographs in FIG. 2 show that the spherulite size is much smaller for the polypropylene which contains tri-naphthylidene sorbitol than for polypropylene alone.

MEASUREMENT OF NMR SHIFTS FOR ACETAL HYDROGENS

The chemical shifts in the NMR for the hydrogens of the —CH— group of the acetal moieties of the following tri-acetal polyol are noted below.

| trinaphthylidene (in pyridine D-5) | |
|---|---|
| 96% isomer₁ | 4% isomer₂ |
| 6.79 ppm | 6.54 ppm |
| 6.58 ppm | 6.50 ppm |
| 6.48 ppm | 6.42 ppm |
| m.p. 250.1 | m.p. 251.3 |

The melting points for the above isomers were determined using a Metler FP61 melting point instrument. The % error is about ±0.2.

What is claimed is:

1. A triacetal polyol compound of a condensation product of a polyol having at least six carbons and at least six hydroxyl groups and an aldehyde having the formula

wherein A is a monovalent radical derived from an unsubstituted or substituted monocyclic or polycyclic compound; said monocyclic compound being selected from compounds which do not form a aldehyde having a benzene ring bonded directly to the carbonyl of the aldehyde.

2. The compound of claim 1 wherein A is aromatic.

3. The compound of claim 2 wherein A is a monovalent hydrocarbon radical derived from a polycyclic compound.

4. The compound of claim 3 wherein the polycyclic compound forming A has one or more ring hydrogens substituted with X, wherein X is selected from the group consisting of —OH, —SH, —OR, —SR, R, Cl, —COOH and —COOR; R being a hydrocarbon radical having up to about 20 carbons.

5. The compound of claim 4 wherein A is a polycyclic compound having at least two rings fused together.

6. The compound of claim 5 wherein A is derived from a polycyclic compound having at least two aromatic rings.

7. The compound of claim 1 wherein A is a monovalent radical derived from naphthalene, phenanthrene, anthracene, guingxaline, fluorene, benzofuran or quingline.

8. The compound of claim 1 wherein A is derived from napthalene, anthracene and phenanthrene.

9. The compound of claim 1 wherein said polyol is a reduced sugar.

10. A mixture comprising two isomers of a compound of a condensation product of a (i) a polyol having at least six carbons and at least six hydroxyl groups and (ii) an aldehyde having the formula

wherein a is a monovalent hydrocarbon radical derived from an unsubstituted or substituent monocyclic or polycyclic compound.

11. The mixture of claim 10 wherein the mixture comprises at least about 50 percent of the isomer which when added to a polyolefin increases the $T_{cc}$ of the polyolefin more than the other isomer when added to the same polyolefin.

12. The mixture of claim 10 wherein the mixture comprises at least about 75 percent of the isomer which when added to a polyolefin increases the $T_{cc}$ of the polyolefin more than the other isomer when added to the same polyolefin.

13. The mixture of claim 10 wherein the mixture comprises at least about 90 percent of the isomer which when added to a polyolefin increases the $T_{cc}$ of the polyolefin more than the other isomer when added to the same polyolefin.

14. A composition comprising (a) one or more polyolefins and (b) the compound of claim 1.

15. A composition comprising (a) one or more polyolefins and (b) the mixture of claim 10.

16. A process for enhancing the rate of crystallization of polyolefin as measured by the $T_{cc}$ of the polymer which comprises adding to a polyolefin an effective amount of the compound of claim 1.

17. A process for enhancing the rate of crystallization of a polyolefin, as measured by the $T_{cc}$ amount of the mixture of claim 10.

18. An article formed totally or in part from a composition comprising (a) one or more polyolefins and (b) the compound of claim 1.

19. An article formed totally or in part from a composition comprising (a) one or more polyolefins and (b) the mixture of claim 11.

20. The isomer of the compound of claim 1 which when added to a polyolefin increases the $T_{cc}$ of the polyolefin more than the other isomer when added to the same polyolefin.

21. The compound of claim 1 wherein the polyol is sorbitol.

22. The isomer of the compound of claim 21 which when added to a polyolefin increases the $T_{cc}$ of the polyolefin more than the other isomer when added to the same polyolefin.

23. A composition comprising (a) one or more polyolefins and (b) a triacetal polyol compound of a condensation product of a polyol having at least six carbons and at least six hydroxyl groups and an aldehyde having the formula

wherein A is a monovalent hydrocarbon radical derived from an unsubstituted or substituted monocyclic or polycyclic compound.

24. A composition comprising (a) one or more polyolefins and (b) a triacetal polyol compound of a condensation product of a polyol having at least six carbons and at least six hydroxyl groups and an aldehyde having the formula

wherein A is a monovalent hydrocarbon radical.

25. The composition of claim 24 wherein A is derived from a hydrocarbon having less than about 25 carbons.

26. The composition of claim 24 wherein the triacetal polyol compound is the trans isomer of of said compound.

27. The compound of claim 22 wherein A is derived from naphthalene.

28. The compound of claim 1 wherein A is a monovalent hydrocarbon radical of naphthalene.

29. The compound of claim 28 wherein said polyol is sorbitol.

30. The compound of claim 28 wherein said polyol is sorbitol.

31. The trans isomer of the compound of claim 30.

32. The isomer of the compounds of claim 21 which when added polypropylene increases the $T_{cc}$ of the polypropylene more than the other isomer when added.

33. The composition of claim 23 wherein said polyolefin is polypropylene.

34. The composition of claim 33 wherein said triacetal polyal compound is formal from a sorbitol and an aldelyde having formula:

wherein a is a unsubstituted or substituted polycyclic compound.

35. The composition of claim 34 wherein a is monovalent hydrocarbon radical of naphthalene.

36. The mixture of claim 10 wherein the mixture comprises at least 50 percent of the isomer which when added to polypropylene increases the $T_{cc}$ of the polypropylene more than the other isomer when added.

37. The composition of claim 33 wherein A is a monovalent hydrocarbon radical derived from unsubstituted or substituted benezene.

38. The composition of claim 37 wherein said polyol is sorbitol.

* * * * *